US00PP36189P2

(12) United States Plant Patent
Star

(10) Patent No.: US PP36,189 P2
(45) Date of Patent: Oct. 8, 2024

(54) ***SANGUISORBA* PLANT NAMED 'Strawberry Dream'**

(50) Latin Name: *Sanguisorba officinalis*
Varietal Denomination: Strawberry Dream

(71) Applicant: Jan Star, Rijnsburg (NL)

(72) Inventor: Jan Star, Rijnsburg (NL)

(73) Assignee: IP—PLANTS B.V., Sassenheim (NL)

( * ) Notice: Subject to any disclaimer, the term of this patent is extended or adjusted under 35 U.S.C. 154(b) by 0 days.

(21) Appl. No.: 18/406,109

(22) Filed: Jan. 6, 2024

(30) Foreign Application Priority Data

Nov. 7, 2023 (QZ) ..... PBR 2023/2312

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

The new cultivar of *Sanguisorba* plant named 'Strawberry Dream' that is characterized by its late flowering season, its inflorescences and stems that are equal in height, and its compact plant habit.

2 Drawing Sheets

Botanical classification: *Sanguisorba officinalis*.
Variety denomination: 'Strawberry Dream'.

CROSS REFERENCE TO A RELATED APPLICATION

This application claims priority to European Community Plant Variety Office (CPVO) Plant Breeder's Rights Application No. 2023/2312 filed on Nov. 7, 2023, under 35 U.S.C. 119(f), the entire contents of which is incorporated by reference herein. The information for the Plant Breeders' Right Application was obtained directly from the Inventor.

BACKGROUND OF THE INVENTION

The present invention relates to a new and distinct cultivar of *Sanguisorba officinalis* and will be referred to hereafter by its cultivar name, 'Strawberry Dream'. 'Strawberry Dream' represents a new burnet, an herbaceous perennial grown for landscape use.

The Inventor discovered the new cultivar in August of 2013 as a naturally occurring branch mutation of *Sanguisorba* 'Rising Star' (not patented) that was growing in a production field of 'Rising Star' in Rijnsburg, The Netherlands.

Asexual propagation of the new cultivar was first accomplished by division in December of 2015 by the Inventor in Rijnsburg, The Netherlands. Asexual propagation by division has determined that the new cultivar is stable and reproduced true to type in successive generations.

SUMMARY OF THE INVENTION

The following traits have been repeatedly observed and represent the characteristics of the new cultivar. These attributes in combination distinguish 'Strawberry Dream' as a unique cultivar of *Sanguisorba*.

1. 'Strawberry Dream' exhibits a late flowering season.
2. 'Strawberry Dream' exhibits inflorescences and stems that are similar in height.
3. 'Strawberry Dream' exhibits a compact plant habit.

The parent plant of 'Strawberry Dream' differs from 'Strawberry Dream' in having a much taller plant height. 'Strawberry Dream' can be most closely compared to *Sanguisorba officinalis* cultivars 'Red Dream' (U.S. Plant Pat. No. 32,441) and 'Arnhem' (not patented). Both 'Red Dream' and 'Arnheim' are both similar to 'Strawberry Dream' in plant habit and flower color. 'Red Dream' differs from 'Strawberry Dream' in having an earlier flower period and a taller plant height. 'Arnheim' differs from 'Strawberry Dream' in having an earlier flowering period, a taller plant height, and a more densely branched habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Holex Flower, OZ Export, Triangle Dream, Heyl, and Floral Market.

BRIEF DESCRIPTION OF THE DRAWINGS

The accompanying color photographs illustrates the overall appearance and distinct characteristics of the new *Sanguisorba*. The photographs were taken of a one-year-old plant of the new cultivar as field grown outdoors in Rijnsburg, The Netherlands and placed in a 30-cm container for the photographs.

The photograph in FIG. 1 illustrates the overall plant habit and appearance of 'Strawberry Dream' in bloom.

Figure 1:
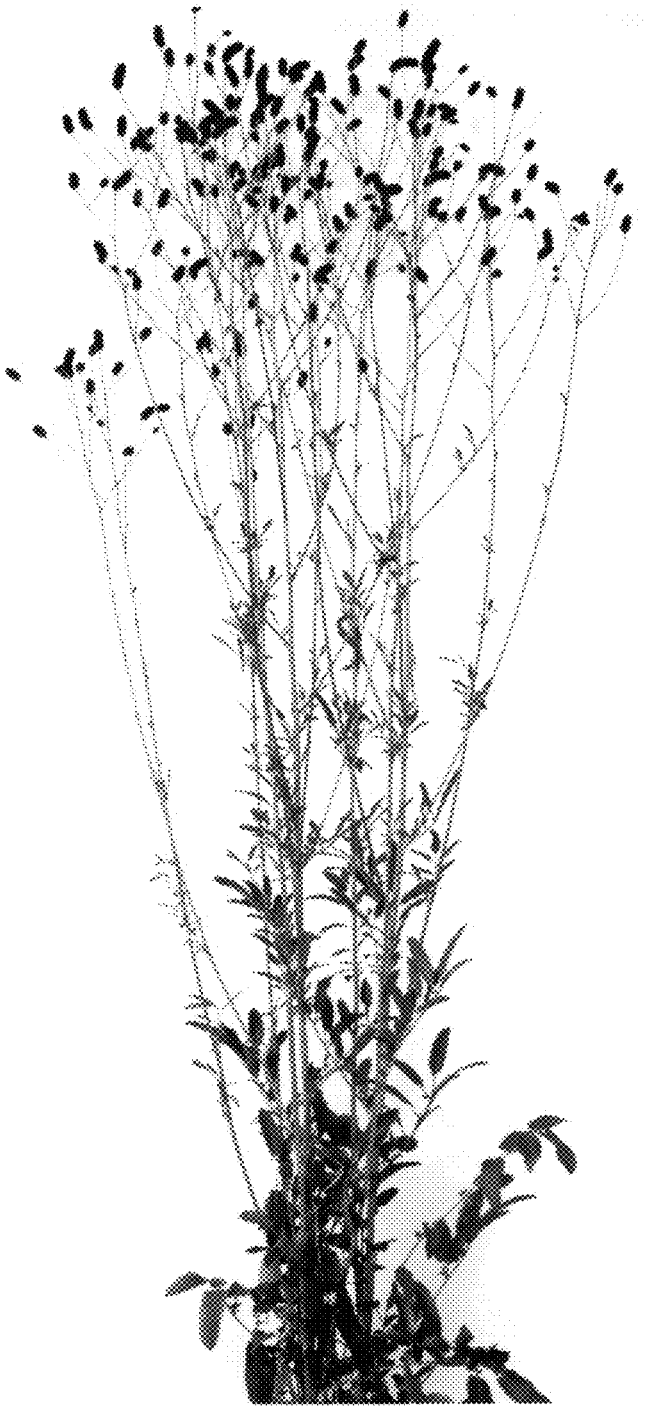
Figure 2:
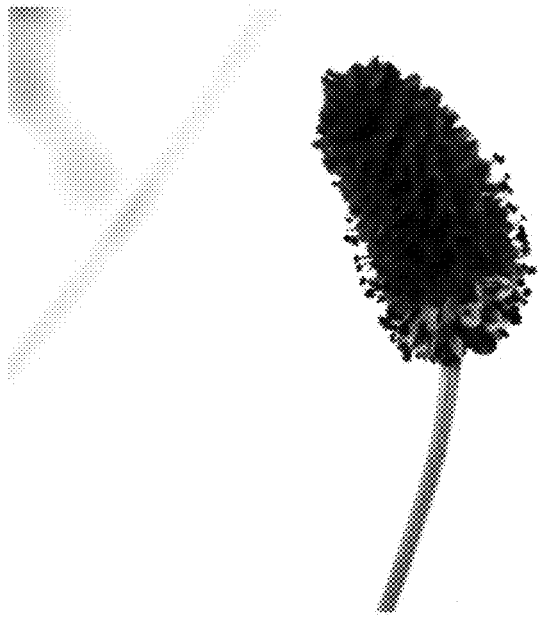

The photograph in FIG. 2 provides a close-up view of an inflorescence of 'Strawberry Dream'.

Figure 3:
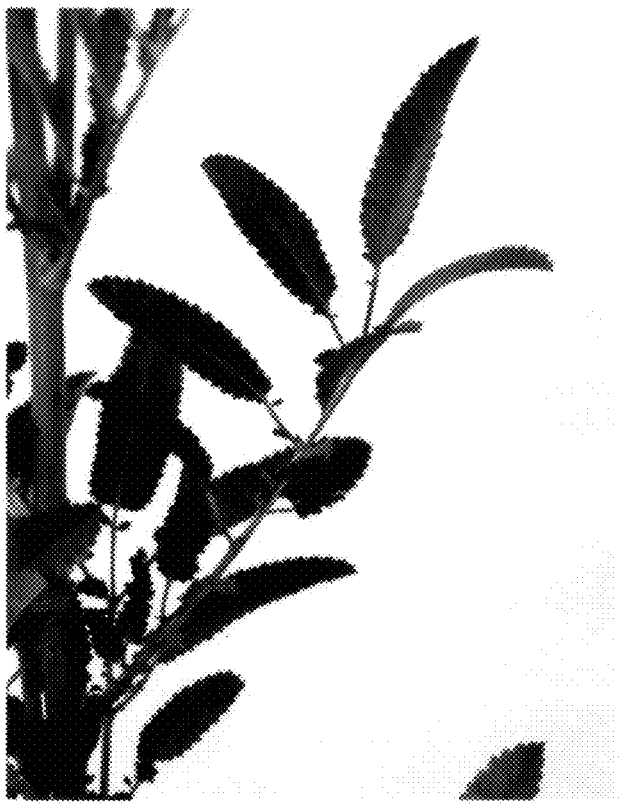

The photograph in FIG. 3 provides a close-up view of the foliage of 'Strawberry Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands and then potted into a 30-cm container for the description. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid August through the end of August in The Netherlands.

*Plant shape*.—Oblong, upright.

*Plant habit*.—Herbaceous perennial.

*Height and spread*.—Average of 1.5 m in height and 54 cm in spread as a one-year-old plant in the landscape.

*Hardiness*.—At least in U.S.D.A. Zones 4 to 9.

*Diseases and pests*.—No susceptibility or resistance to diseases or pests has been observed.

*Root description*.—Dense, smooth and glabrous surface, shallow and deep, 164C in color.

*Root development*.—A young fully rooted plant is produced in 10 to 12 weeks from a bare root division.

*Propagation*.—Division.

*Growth rate*.—Moderate.

Stem description:

*Shape*.—Round, moderately angled.

*Stem color*.—Young; 138A, mature; 146A.

*Stem size*.—Up to 1.5 m in length and 6 mm in diameter.

*Stem aspect*.—Average of 10° to vertical (varying between 0° and 20°).

*Stem surface*.—Slightly glossy.

*Internode length*.—6.7 cm.

*Branching*.—Average of 3 main branches and 23 lateral branches per plant.

Foliage description:

*Leaf shape*.—Narrow obovate.

*Leaf division*.—Compound; imparipinnate.

*Leaf quantity*.—an average of 15 leaflets per leaf (ranges from 23 leaflets on the lower leaves to 5 leaflets on the upper leaves).

*Leaf base*.—Truncate on lower leaves and attenuate on upper leaves.

*Leaf apex*.—Acute.

*Leaf aspect*.—Slightly to moderately carinate.

*Leaf arrangement*.—Alternate.

*Leaf size*.—Average of 16.7 cm in length (including petiole), 8.3 cm in width.

*Leaf attachment*.—Petiolate.

*Leaflet*.—Lanceolate to narrow oblong in shape, terminal leaflets; average of 5.6 cm in length, 1.7 cm in width, lateral leaflets; average of 4.1 cm in length and 1.5 cm in width, acute apex, base is truncate on lower leaves and attenuate on upper leaves.

*Leaflet venation*.—Pinnate, upper surface color 144A, lower surface 147D.

*Leaflet margins*.—Dentate to serrate.

*Leaflet surface*.—Both surfaces smooth and glabrous, upper surface slightly glossy, lower surface matte.

*Leaflet color*.—Young upper surface 137B, young lower surface 138B, mature upper surface NN137B, mature lower surface a blend of 138A and 147B.

*Rachis (petiole) and petiolule*.—Rachis (petiole); average of 9.5 cm in length, 2 mm in diameter, petiolule of tip leaflet; average of 1.7 cm in length and 1 mm in diameter, petiolule of lateral leaflet; average of 1.1 cm in length and 1 mm in diameter, surfaces are smooth, glabrous, slightly glossy, strong, upper surface color 146A to 146B, petiolules are 146B, tinged 181A, lower surface 145A, petiolules are 145A, occasionally tinged 145C.

*Stipules*.—At the base of each leaf is a leafy stipule on each side, falcate in shape, 2.3 cm in length, 9.5 mm in width, surfaces smooth and glabrous, dentate to serrate margins, acute tip, base is broadly cuneate, color upper surface NN137B, color lower surface a blend of 138A and 147B, at the base of each petiolule a leafy stipule is present on each side, ovate to orbicular in shape, 7 mm in length and width, both surfaces smooth and glabrous with upper side slightly glossy, upper surface NN137B in color, lower surface a blend of 138A and 147B in color.

Inflorescence description:

*Type*.—Terminal panicles of elongated ovoid to oblong shaped spikes comprised of numerous, densely packed flowers, determinate.

*Inflorescence size*.—Panicle; 29.8 cm in height, 21.4 cm in diameter, spike; 2.2 cm in height, 9 mm in diameter.

*Fragrance*.—Moderately strong and unpleasant.

*Flower lastingness*.—Average of 14 days, persistent.

*Flower quantity*.—Average of 175 flowers per spike, over 36,400 flowers and buds per plant.

*Flower aspect*.—Rotate, single, outward and freely flowering.

*Flower size*.—Average of 2 mm in height and diameter, 3 mm in depth.

*Peduncle*.—Average of 21.9 cm in length, 1.5 mm in diameter, held in a vertical angle, secondary 45°, strong, smooth and glabrous, slightly glossy, 146A in color.

*Bud description*.—Average of 2 mm in length, 1.2 mm in diameter, obovate in shape, smooth, glabrous, and matte surface, color; 185B, axially striped N186C, base 145C and 145D.

*Petals*.—Rotate, cruciform, average of 4, 1 row, unfused, 2 mm in length, 1 mm in width, ovate in shape, moderately concave, tip is acute, broadly cuneate base, entire margins, both surfaces glabrous, slightly velvety and matte, color; when opening and fully open upper surface N155A, blotched in the center with N148A and 200C, veins N186C, when opening and fully open lower surface N186C, margins N155A, veins N186C, upper and lower surface when fading 187A, broad margins 187D.

*Calyx*.—Rotate, cruciform, average of 1 mm in length and diameter.

*Sepal*.—An average of 4 in 1 row, average of 1 mm in length and 0.75 mm in width, ovate in shape, acute tip, cuneate base, entire margins, color; when opening and fully open upper and lower surface 196A, both surfaces are matte, upper surface smooth, glabrous, lower surface densely pubescent with soft short hairs an average of 0.2 mm in length, 157D in color.

*Flower bracts*.—None.

Reproductive organs:

*Gynoecium*.—Pistil: 1, average of 1.5 mm in length, stigma; flattened and club-shaped, 0.3 mm in length and in diameter, N79A in color, style; average of 1.2 mm in length, N79B in color, base N79D, ovary; 195C in color.

*Androecium*.—Stamens; average of 4, filament; 1.75 mm in length, N155B in color, anthers; short, kidney-shaped, 0.5 mm in length, 0.3 mm in width, 200A in color, pollen; low in quantity, 17B in color.

*Fruit/seed*.—None observed.

It is claimed:

1. A new and distinct cultivar of *Sanguisorba* plant named 'Strawberry Dream' as herein illustrated and described.

* * * * *